United States Patent
Yang et al.

(10) Patent No.: US 10,945,709 B2
(45) Date of Patent: Mar. 16, 2021

(54) SYSTEMS, METHODS AND COMPUTER READABLE STORAGE MEDIA STORING INSTRUCTIONS FOR IMAGE-GUIDED INTERVENTIONS BASED ON PATIENT-SPECIFIC MODELS

(71) Applicant: Emory University, Atlanta, GA (US)

(72) Inventors: Xiaofeng Yang, Atlanta, GA (US); Tian Liu, Atlanta, GA (US)

(73) Assignee: Emory University, Atlanta, GA (US)

( * ) Notice: Subject to any disclaimer, the term of this patent is extended or adjusted under 35 U.S.C. 154(b) by 1425 days.

(21) Appl. No.: 15/050,109

(22) Filed: Feb. 22, 2016

(65) Prior Publication Data
US 2016/0242745 A1 Aug. 25, 2016

Related U.S. Application Data

(60) Provisional application No. 62/119,097, filed on Feb. 20, 2015.

(51) Int. Cl.
*A61B 8/08* (2006.01)
*A61B 5/055* (2006.01)
(Continued)

(52) U.S. Cl.
CPC .......... *A61B 8/5261* (2013.01); *A61B 5/055* (2013.01); *A61B 8/08* (2013.01); *A61B 8/12* (2013.01);
(Continued)

(58) Field of Classification Search
CPC .......... A61B 8/5261; A61B 8/08; A61B 8/12; A61B 8/4209; A61B 8/4245; A61B 8/483;
(Continued)

(56) References Cited

U.S. PATENT DOCUMENTS

2003/0167005 A1* 9/2003 Sakuma ............... A61B 5/489
600/443
2005/0033173 A1* 2/2005 Von Behren .......... A61B 8/00
600/443
(Continued)

OTHER PUBLICATIONS

Yang et al., Ultrasound 2D Strain Estimator Based on Image Registration for Ultrasound Elastography, Proc SPIE Int Soc Opt Eng. Mar. 20, 2014; 9040: . doi:10.1117/12.2043865. (Year: 2014).*
(Continued)

*Primary Examiner* — Amelie R Davis
*Assistant Examiner* — John Denny Li
(74) *Attorney, Agent, or Firm* — Emory Patent Group

(57) ABSTRACT

Systems, methods, and computer-readable storage media relate to generate an integrated image based on strain data and elastic model. The method may include determining, by a processor, a range of probe positions for placement of an ultrasound probe with respect to a patient based on strain data, the range of positions including a first position, a second position, and one or more positions there between. The method may also include acquiring 3D TRUS images of the patient at each of the one or more positions of the range and generating a patient specific biomechanical model based on the 3D TRUS images. The method may further include integrating the patient specific biomechanical model, the 3D TRUS images and MR images to generate an integrated image of the prostate. The methods, systems, and computer readable media can improve efficiency and accuracy of 3D TRUS and MR image registration, e.g., for image-guided interventions.

17 Claims, 6 Drawing Sheets

(51) Int. Cl.
  *A61B 8/00*   (2006.01)
  *G16H 50/50*  (2018.01)
  *A61B 8/12*   (2006.01)
  *A61B 6/03*   (2006.01)
  *A61B 6/00*   (2006.01)

(52) U.S. Cl.
  CPC .......... *A61B 8/4209* (2013.01); *A61B 8/4245* (2013.01); *A61B 8/483* (2013.01); *A61B 8/485* (2013.01); *A61B 8/5223* (2013.01); *G16H 50/50* (2018.01); *A61B 6/032* (2013.01); *A61B 6/037* (2013.01); *A61B 6/488* (2013.01); *A61B 6/5247* (2013.01); *A61B 2576/00* (2013.01)

(58) Field of Classification Search
  CPC ....... A61B 8/485; A61B 8/5223; A61B 5/055; A61B 6/032; A61B 6/037; A61B 6/488; A61B 6/5247; A61B 2576/00; G16H 50/50
  See application file for complete search history.

(56) References Cited

U.S. PATENT DOCUMENTS

| | | | |
|---|---|---|---|
| 2005/0187473 A1* | 8/2005 | Boctor | A61B 8/485 600/437 |
| 2012/0128223 A1* | 5/2012 | Rivaz | A61B 8/485 382/131 |
| 2013/0064439 A1 | 3/2013 | Khurd et al. | |
| 2013/0324841 A1* | 12/2013 | Kamen | A61B 8/0841 600/424 |
| 2016/0310761 A1* | 10/2016 | Li | G06K 9/52 |

OTHER PUBLICATIONS

Fedorov et al. "Image Registration for Targeted MRI-guided Transperineal Prostate Biopsy." Journal of Magnetic Resonance Imaging, Oct. 2012; 36(4): 987-992.

Hadaschik et al. "A Novel Stereotactic Prostate Biopsy System Integrating Pre-Interventional Magnetic Resonance Imaging and Live Ultrasound Fusion." The Journal of Urology, Dec. 2011; 186:2214-2220.

Hu et al. "MR to ultrasound registration for image-guided prostate interventions." Medical Imaging Analysis 2012; 16:687-703.

Mitra et al. "Prostate multimodality image registration based on B-splines and quadrature local energy." International Journal of Computer Assisted Radiology, 2012; 7:445-454.

Moradi et al. "Two Solutions for Registration of Ultrasound to MRI for Image-Guided Prostate Interventions." Conference Proceedings: Annual International Conference of IEEE Engineering in Medicine and Biology Society. IEEE Engineering in Medicine and Biology Society. Annual Conference, 2012; 2012:1129-1132.

Mousavi et al. "Towards ultrasound probe positioning optimization during prostate needle biopsy using pressure feedback." International Journal of Computer Assisted Radiology, 2013; 8:1053-1061.

Selmi et al. "3D Interactive Ultrasound Image Deformation for Realistic Prostate Biopsy Simulation." 6th International Symposium in Biomedical Simulation; Strasbourg, France: Springer Verlag. 2014; pp. 122-130.

Van De Ven et al."Surface-based prostate registration with biomechanical regularization." Proceedings of SPIE Medical Imaging, 2013; 86711:86711R.

Wang et al. "Towards Personalized Biomechanical Model and MIND-Weighted Point Matching for Robust Deformable MR-TRUS Registration." Computer-Assisted and Robotic Endoscopy; Springer. 2014; pp. 121-130.

* cited by examiner

500

600

SYSTEMS, METHODS AND COMPUTER READABLE STORAGE MEDIA STORING INSTRUCTIONS FOR IMAGE-GUIDED INTERVENTIONS BASED ON PATIENT-SPECIFIC MODELS

CROSS REFERENCE TO RELATED APPLICATION

This application claims priority to Provisional Application Ser. No. 62/119,097 filed Feb. 20, 2015, which is hereby incorporated by reference in its entirety.

BACKGROUND

Prostate cancer is one of the major international health problems with a large and rising incidence in many parts of the world. Transrectal ultrasound (TRUS) has been the standard imaging modality for image-guided interventions (e.g., biopsy and radiotherapy) for detecting, treating and/or monitoring prostate cancer due to its versatility and real-time capability. However, TRUS may not reliably identify prostate cancer and thus the cancerous regions often cannot be well-targeted during these interventions.

In the past decade, magnetic resonance (MR) imaging has shown promise in visualizing prostate tumors with high sensitivity and specificity for the detection of early-stage prostate cancer. Developments in MR-targeted, TRUS-guided techniques, in particular, have increased clinical interests because the ability to incorporate MR-targeted cancer-bearing regions into TRUS-guided prostate procedures can provide extremely important benefits in terms of more successful prostate-cancer diagnosis and treatment. However, MR-TRUS image registration can be challenging due to the intrinsic differences in the grey-level intensity characteristics between the two image modalities and the presence of artifacts, particularly on TRUS images.

SUMMARY

Thus, there is a need for accurate and efficient registration of the MRI and ultrasound prostate images that can be used for interventional procedures, such as prostate-cancer diagnosis and treatment.

This disclosure generally relates to methods, systems, and computer readable storage media that include instructions to integrate MR and ultrasound images, for example, for interventional procedures based on a generated patient specific biomechanical model.

In some embodiments, the methods may relate to a computer-implemented method for generating an integrated image of a prostate of a patient. In some embodiments, the method may include determining, by a processor, a range of probe positions for placement of an ultrasound probe with respect to a patient based on strain data. The range of probe positions may include a first probe position, a second probe position, and one or more probe positions between the first probe position and the second probe position. The method may further include acquiring 3D TRUS images of the patient at each of the one or more probe positions of the range and generating a patient specific biomechanical model based on the 3D TRUS images. The method may also include integrating the patient specific biomechanical model, the 3D TRUS images and MR images to generate an integrated image of the prostate. In further embodiments, the method may further include displaying the integrated image, for example, for use in image-guided interventions (e.g., biopsy, radiotherapy, among others).

In some embodiments, the systems may relate to a system generating an integrated image of a prostate of a patient. In some embodiments, the system may include an ultrasound system that includes an ultrasound probe, an ultrasound stepper configured to hold and move the ultrasound probe, and an image acquisition device configured to acquire 2D and 3D ultrasound images. The system may also include a processor and a memory. In some embodiments, the processor may be configured to determine a range of probe positions for placement of the ultrasound probe with respect to a patient based on strain data. The range of positions may include a first probe position, a second probe position, and one or more probe positions between the first probe position and the second probe position. In some embodiments, the processor may be further configured to acquire 3D TRUS images of the patient at each of the one or more probe positions of the range and generate a patient specific biomechanical model based on the 3D TRUS images. In some embodiment, the processor may also be configured to integrate the patient specific biomechanical model, the 3D TRUS images and MR images to generate an integrated image of the prostate.

In some embodiments, the computer-readable media may relate to a non-transitory computer-readable medium storing instructions thereon, wherein the instructions are executable by a computer to cause the computer to generate an integrated image of a prostate of a patient. In some embodiments, the instructions may include determining, by a processor, a range of probe positions for placement of an ultrasound probe with respect to a patient based on strain data. The range of probe positions may include a first probe position, a second probe position, and one or more probe positions between the first probe position and the second probe position. The instructions may further include acquiring 3D TRUS images of the patient at each of the one or more probe positions of the range and generating a patient specific biomechanical model based on the 3D TRUS images. The instructions may also include integrating the patient specific biomechanical model, the 3D TRUS images and MR images to generate an integrated image of the prostate. In further embodiments, the instructions may further include displaying the integrated image.

Additional advantages of the disclosure will be series forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
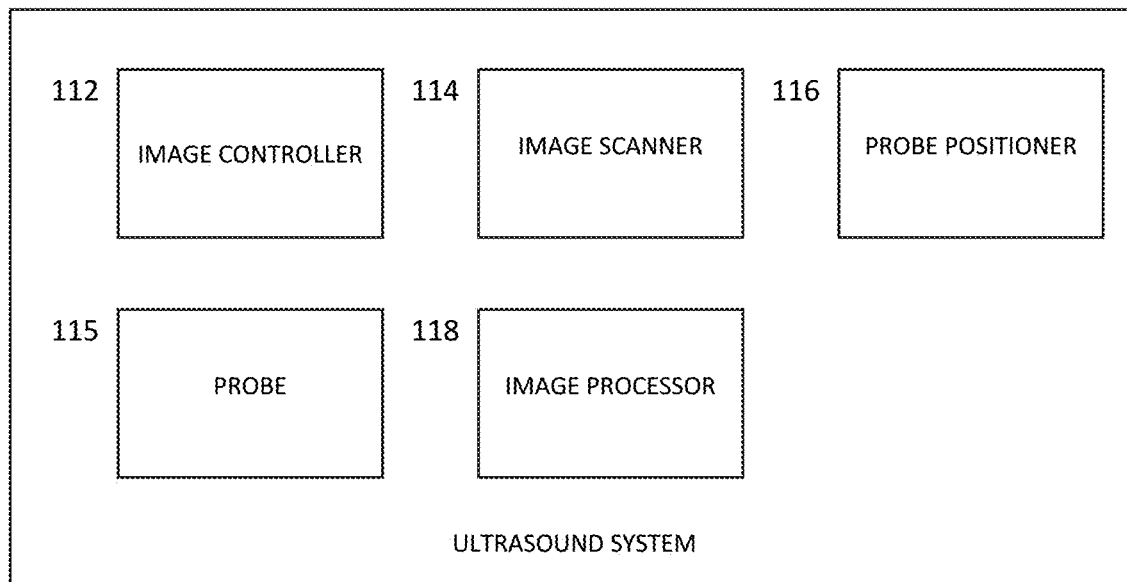
FIG. 1 shows a block diagram illustrating a system according to embodiments.
Figure 1:
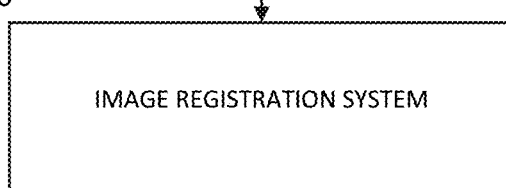
Figure 1:
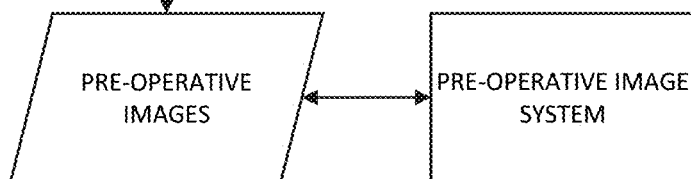

In the following description, numerous specific details are series forth such as examples of specific components, devices, methods, etc., in order to provide an understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

This disclosure generally relates to methods, systems, and computer readable storage media that accurately and efficiently generate an integrated image including the ultrasound image data and pre-operative image (MR) data based on a generated patient-specific biomechanical model. This disclosure incorporates patient-specific elastic data provided by the patient-specific biomechanical model into the registration framework to allow an inhomogeneous elastic map to be assigned to prostate volume deformation. This disclosure thereby address the deficiencies of integrating ultrasound and pre-operative image data by avoiding image dissemblance between different imaging modalities.

The methods, systems, and computer readable media according to embodiments can improve the accuracy of the patient specific biomedical model and registration of the image modalities by determining the optimal range of positions of the ultrasound probe for capturing the ultrasound images to be used for registration and the patient-specific biomechanical model. The disclosure can determines the optimal position(s) of the ultrasound probe by determining probe positions at which the deformation can considered to be predictable. This can thereby improve registration time and accuracy.

The embodiments of the disclosure are described with respect to a prostate of a human patient. It should be understood by one of ordinary skill in the art that the embodiments of the disclosure can be applied to other targets (such as other portions of the body), whether human or animal. For example, other targets may include liver and kidney. Additionally, the disclosure is discussed with respect to TRUS and MR images. However, it will be understood that the disclosure can be used with other imaging modalities. For example, it can be used with Positron Emission tomography (PET)/MR and PET/computer tomography (CT) systems. The uses of the methods and systems of the embodiments of the disclosure can also be adapted for other procedures.

FIG. 1 shows an example of a system 100 for generating planning images based on pre-operative image data (e.g., MR images) and ultrasound image data (e.g., TRUS images).

In some embodiments, the modules and/or systems of the system 100 may be connected to a data network, a wireless network, or any combination thereof. In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture. Although the modules of the system are shown as being directly connected, the modules may be indirectly connected to one or more of the other modules of the system. In some embodiments, a module may be only directly connected to one or more of the other modules of the system.

As shown in FIG. 1, the system 100 may include an ultrasound imaging system 110. In some embodiments, the ultrasound (US) imaging system 110 may be configured to acquire two dimension (2D) and/or three-dimensional (3D) ultrasound images. In some embodiments, for example, the ultrasound system 110 may include a TRUS ultrasound image system.

In some embodiments, the ultrasound image system 110 may include an image controller 112, an image scanner 114, an ultrasound probe 115, a probe positioner 116, and an image processor 118. The image controller 112 may be configured to control the image scanner 114, the probe 115, and/or the probe positioner 116. In some embodiments, the probe positioner 116 may be a stepper that includes a mechanical probe holder. The probe positioner 116 may be configured to move the probe 115 in at least the y direction (the anterior-posterior direction relative to the patient, for example, in a lithotomy position), z direction (superior-inferior direction relative to the patient), and/or x direction (the right-left direction relative to the patient). In some embodiments, the image processor 118 may be configured to process the image data acquired to generate 2D and/or 3D ultrasound images. In some embodiments, the ultrasound image system 110 may include an image acquisition device. The image acquisition device may include the image processor, the image controller, or a combination thereof.

The system 100 may include a pre-operative image system 132 and/or pre-operative image data 130, for example, stored in an image data database. In some embodiments, the pre-operative image data may be MR images of the target (e.g., prostate) of the patient. The pre-operative image system may be a MR system configured to acquire MR images of the target of the patient. In other embodiments, the pre-operative image data and/or pre-operative image system may be another image modality, such as PET/CT and/or PET/MR.

In some embodiments, the system 100 may include an image integration system 120 configured to integrate the image data acquired by systems 110 and/or 132. The image integration system 120 may be a component of or separate from an ultrasound image system and/or an image-guided interventional system (such as a biopsy system). The system 120 may be configured to acquire the image data from the imaging systems (e.g., 110 and/or 132) and/or a medical imaging database configured to store medical imaging data.

Figure 2:
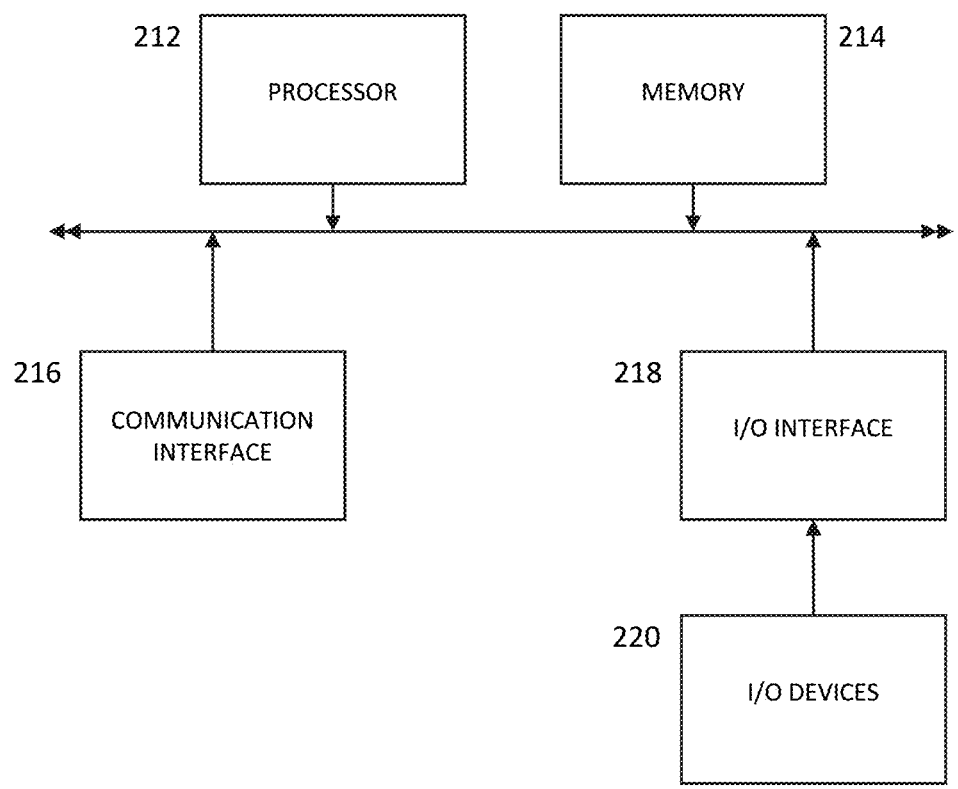
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The processor(s) 212 may be coupled directly or indirectly to one or more computer-readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

The processor(s) 212 may be configured to determine probe position(s), move the stepper, acquire the images, generate the biomechanical model, generate an integrated image, among others, or any combination thereof. In some embodiments, the processor(s) 212 may be capable of performing the image data processing. In other embodiments, the system may include a separate processor(s) (e.g., CPU) for determining probe position(s), moving the stepper, acquiring the images, generating the biomechanical model, and/or generating an integrated image.

In some embodiments, another computer system may assume the data analysis or other functions of the processor(s) 212. In response to commands received from the input device, the programs or data stored in the memory 214 may be archived in long term storage or may be further processed by the processor and presented on a display.

In some embodiments, the system 210 may include a communication interface 216 configured to conduct receiving and transmitting of data between other modules on the system and/or network. The communication interface 216 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 218 configured for receiving information from one or more input devices (e.g., a keyboard, a mouse, and the like) and/or conveying information to one or more output devices (e.g., a printer, a CD writer, a DVD writer, portable flash memory, etc.). In some embodiments, the one or more input devices may configured to control, for example, the acquisition of the TRUS images, movement of the stepper, displaying of the integrated image on a display, printing of the images by a printer interface, among other things.

FIGS. 3, 4, 6 and 7 show methods of generating integrated image data, for example, for interventional-guided systems. The system for carrying out the embodiments of the methods disclosed herein is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel.

Unless stated otherwise as apparent from the following discussion, it will be appreciated that terms such as "identifying," "receiving," "integrating," "filtering," "combining," "reconstructing," "segmenting," "generating," "registering," "determining," "obtaining," "processing," "computing," "selecting," "estimating," "detecting," "moving," "calculating," "comparing," "modifying," "aligning" "fusing," "displaying," "causing," "acquiring," "obtaining," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

Figure 3:
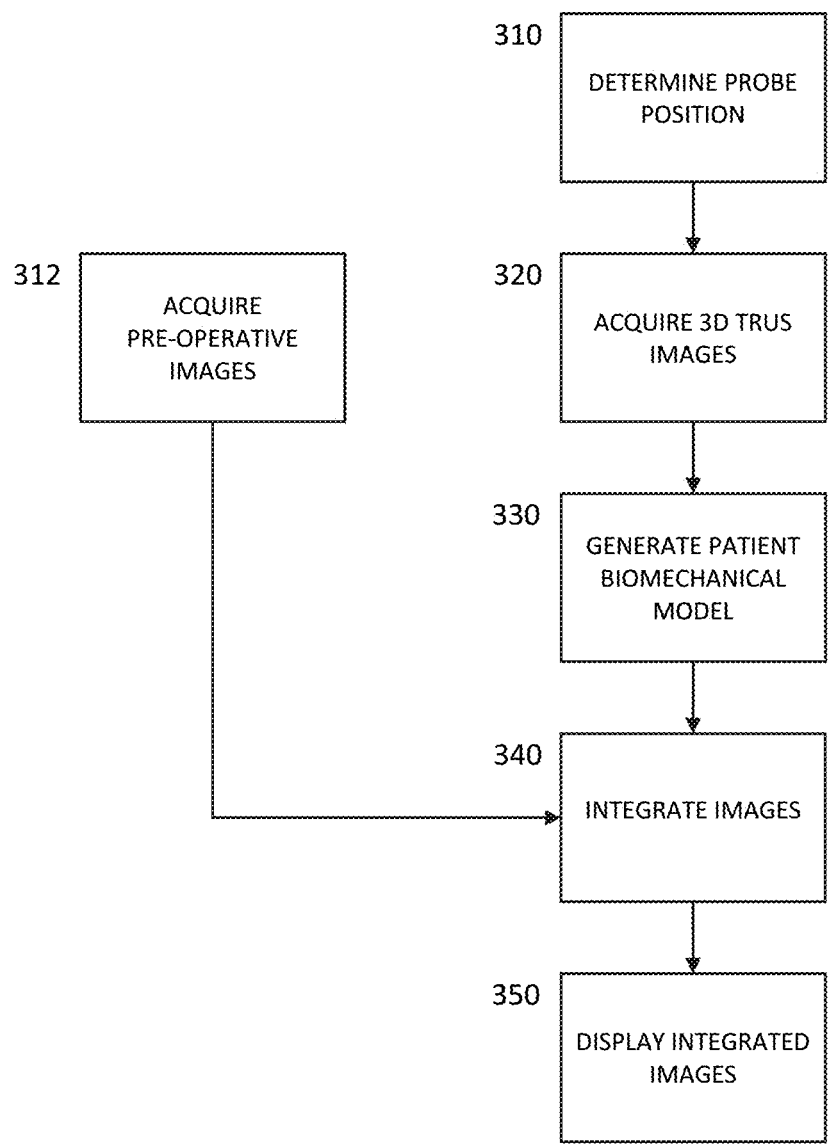
FIG. 3 shows a method of processing ultrasound image data and pre-operative image data to generate an integrated image according to embodiments.

FIG. 3 shows a method 300 for integrating pre-operative image data and TRUS image data according to embodiments. In some embodiments, the method 300 may include a step 310 of determining a range of one or more probe positions in the y direction (e.g., a number of probe positions between a first probe position and a second probe position (e.g., y1 and y2, respectively)) to move the probe via the stepper at which the 3D TRUS images will be acquired by the ultrasound system.

In some embodiments, the method 300 may then include a step 320 of acquiring 3D TRUS images at each y probe position included in the range of probe positions determined in step 310. In some embodiments, multiple 3D TRUS images may be acquired at each image. For example, multiple 3D TRUS images (e.g., 5 3D TRUS images) may be uniformly captured at y probe positions between and including the first and second probe positions, y1 and y2. At each y probe position, the probe can be maintained at the same x position (e.g., $x_0$) and maintained and/or moved in the z direction to obtain the 3D TRUS image.

Next, the method 300 may include a step of 330 of generating a patient-specific biomechanical model based on the acquired 3D TRUS images. In some embodiments, the patient-specific biomechanical model may be an elastic model generated based on strain data determined from the 3D images. After which, the method 300 may include a step 340 of integrating the biomechanical model (step 330), the acquired 3D TRUS images (320), and the pre-operative images (e.g., MR images) (312), to generate integrated MR-TRUS images.

The method 300 may further include a step 350 of outputting the generated integrated image(s). In some embodiments, the outputting may include displaying, printing, storing, and/or transmitting the generated image(s). In some embodiments, the integrated image(s) may be transmitted to another system, server and/or storage device for the printing, displaying and/or storing the generated images. In some embodiments, the method may further include transmitting the generated image(s) to another system. For example, the registered image data may be displayed and used in, for example, image-guided interventional procedures/systems.

Figure 4:
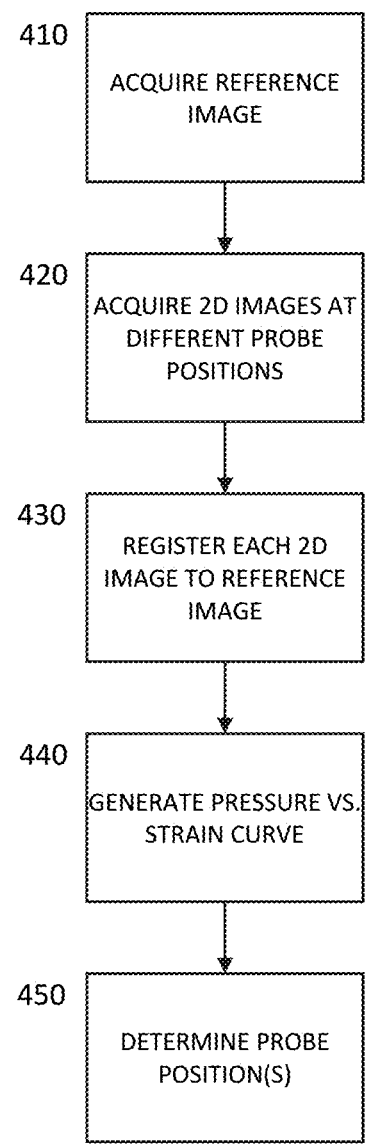
FIG. 4 shows a method of determining a position of a probe for acquiring TRUS images according to some embodiments.

FIG. 4 shows a method 400 for determining a range of one or more positions of the probe (step 310) between and including a first probe position and a second probe position with respect to the stepper for acquiring the 3D images (step 320) according to embodiments. The range of probe positions of the probe may include a first probe position and a second probe position. In some embodiments, the range may also include one or more probe positions between the first probe position and the second probe position.

In some embodiments, the method 400 may include a step 410 of acquiring a 2D reference image. In some embodiments, the reference TRUS image may be acquired after calibration of an ultrasound probe placed into the mechanical holder of the stepper after placement into the rectum for prostate scanning. For example, the calibration may be performed automatically or manually. The calibration can ensure that a prostate is visible as the probe moving from the base to apex (or from apex to base). After calibration, the 2D TRUS reference image may be taken. The image controller may cause the stepper to move the probe to a position that substantially corresponds to the mid-plane of the prostate. The image controller can read this probe position as the initial position ($x_0$, $y_0$, $z_0$). The X position can represent a position in the right-left direction relative to the patient; Y position can represent a position in the anterior-posterior direction relative to the patient; and the Z position a represent a position in the superior-inferior direction. The image controller acquires a 2D image at the initial position. The 2D ultrasound image at the initial position can correspond to the reference image.

After the reference image is acquired (step 420), the image controller can cause the probe positioner (stepper) to move along the y-axis (i.e., up and down) and cause the ultrasound scanner to capture 2D ultrasound images at different y probe positions (e.g., the probe is maintained at the same x position (e.g., $x_0$)). For example, the ultrasound scanner may acquire 2D TRUS images at positions between 0.5 and 2.5 cm in both directions (up and down) from the reference image, depending on the patient anatomy. In some embodiments, the ultrasound scans may be about or below 2 frame/mm.

After the ultrasound images are acquired, the method 400 may include a step 430 of registering the 2D TRUS image(s) captured at each probe position to the 2D TRUS reference image (e.g., the 2D TRUS images captured at the reference probe position). Each probe position in the y direction corresponds to a different pressure. In this step, the deformation of each voxel for each position at which 2D images can be captured.

Next, the method 400 may include a step 440 of generating strain data. The step 440 may include generating strain vs. pressure (probe position) curve for each voxel. For each 2D registration (registration between each 2D image at different y probe position(s) and the reference probe position), a deformation map may be generated. Next, the strain map can be generated from the deformation map. That is, the deformation map can be normalized by the displacement (deformation) that was used for the probe at each position. Each strain map may be calculated from each pair of 2D images (the reference image and the image captured at a different position). In this way, each strain map corresponds to one probe position and each voxel has a serial of corresponding strain values in these strain maps (corresponding to different probe positions).

Next, the strain vs. pressure curve (also referred to as strain data) may be generated from these strain maps for each voxel. The y-axis of strain vs pressure curve can represent the strain value of each voxel in these strain maps and the x-axis can represent the probe positions in the y direction (pressure). For example, if 2D image includes 500 voxels and about 300 voxels are included in prostate, at least 300-400 curves may be generated.

Next, the (optimal) probe position range can be determined from the strain vs. pressure curves. The probe position range can correspond to the linear part of the curve. For example, the upper and lower limits of the range may correspond to the probe positions at and in which at least 80% voxels are in the linear parts of their curves. In this example, at least 80% voxels may have an overlap of linear part in these optimal probe position ranges. It will be understood that the optimal probe position range may be considered a different percentage of overlapping linear parts.

Figure 5:
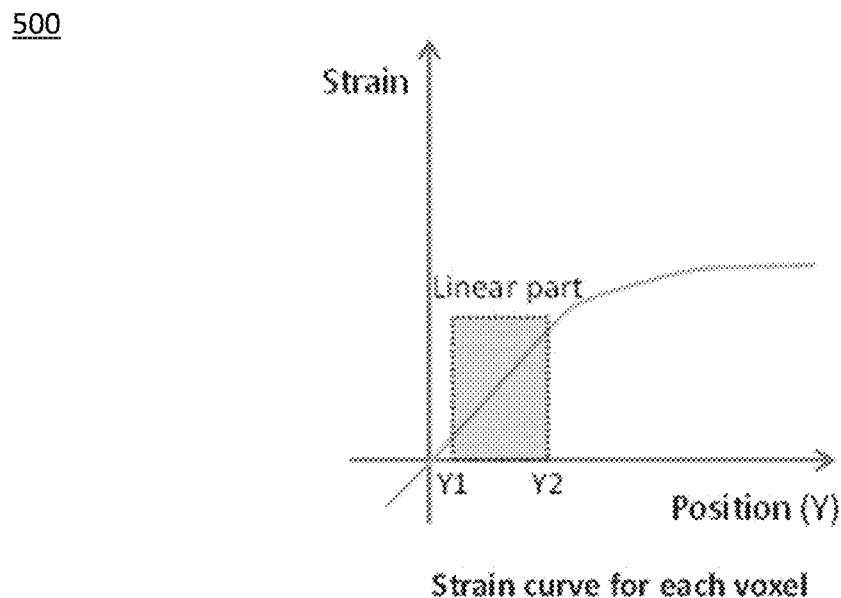
FIG. 5 shows an example of a strain curve for determining a range of one or more probe positions according to embodiments.

FIG. 5 shows an example of a pressure vs. strain curve 500 according to embodiments. The range of probe positions (y1 to y2) corresponds to the range where the strain is linearly related to the pressure applied to the rectal wall or the y position of the probe. In this example, the area of the curve defined by probe positions y1 and y2 represents strain values that are linearly related. In this example, the range of probe positions corresponds to probe positions between and including first probe position y1 and second probe position y2 (the lower and upper limits, respectively). The first 3D image can be captured at probe position y1, the last 3D image can be captured at probe position y2, and a number of images at different positions between probe positions y1 and y2 can be captured. The number of probe positions and increment in between the first and second probe positions (y1 and y2) can vary.

Figure 6:
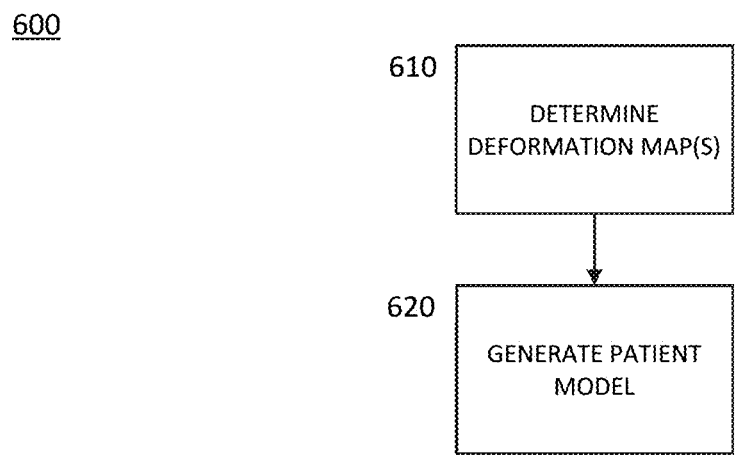
FIG. 6 shows a method of determining an elastic model of a prostate for a patient according to embodiments.

FIG. 6 shows a method 600 for determining a patient specific biomechanical model (step 330)(also referred to as elastic map or model) according to embodiments. After multiple 3D images are acquired under different probe-induced deformation (i.e., different probe positions included in the range)(step 320), the method 600 may then create a patient-specific biomechanical model using the 3D TRUS images.

In some embodiments, the method 600 may include a step 610 of determining deformation maps by mapping each subsequent set of the 3D ultrasound images to a first set of 3D ultrasound images (the 3D TRUS images acquired at probe position x0, y1, z0) to generate multiple deformation maps under the different capturing probe position using a hybrid deformable image registration, combining normalized mutual information (NMI) metric with normalized sum-of-squared-differences (NSSD) metric. In this way, the robustness of the registration can be improved. Next, the method may include generating the patient specific biomechanical model (elastic model) based on the strain data (e.g., multiple strain vs. pressure curves) generated from the 3D ultrasound data captured at the determined (optimal) probe positions. The elastic model for the prostate for a patient can be generated by calculating the strain vs. probe position curves for each voxel in 3D prostate, and determining the slopes (rate of grade) for each voxel of strain-pressure curves.

In other embodiments, the patient specific biomechanical model may be generated according to other methods.

Figure 7:
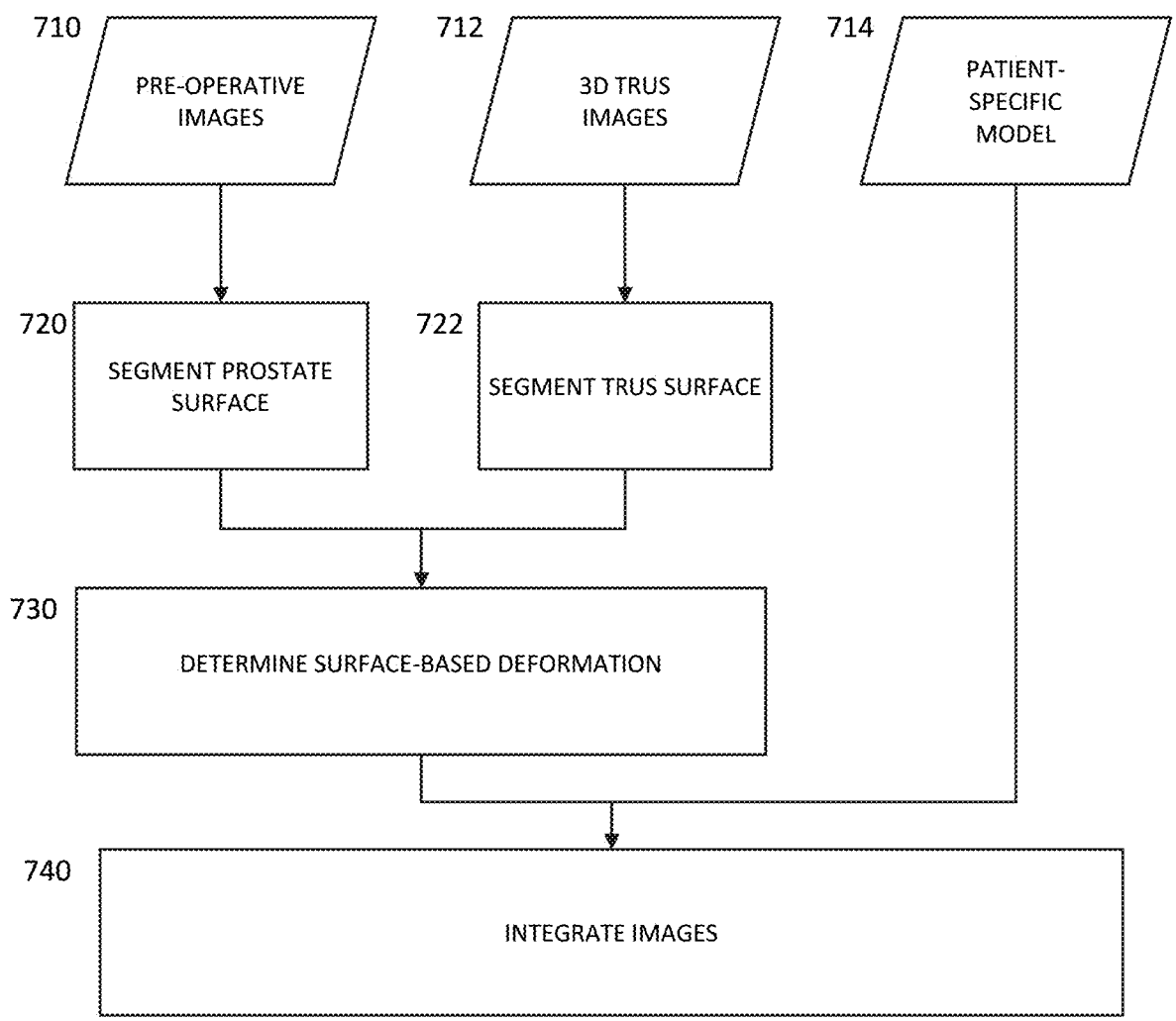
FIG. 7 shows a method of registering TRUS and pre-operative images according to embodiments.

FIG. 7 shows a method 700 for integrating the preoperative images (MR images) and the TRUS 3D ultrasound images based on the determined patient specific biomechanical model (also referred to as elastic model) (step 340). In some embodiments, the method 700 may include a step 720 of performing MRI prostate surface segmentation on the pre-operative images 710 (corresponding to images 312), which can be generated manually or automatically. The method 700 may also include a step 722 of performing ultrasound prostate surface segmentation on the 3D TRUS image data 712 (corresponding to images acquired in step 320), which can be generated manually or automatically.

Next, the method 700 may include a step 730 of determining surface-based deformation by performing surface registration based on the prostate capsules segmented from the MR and TRUS images. Then, a triangular mesh surface can be generated for each prostate surface, with the vertices of the surface selected as the surface landmarks Because each surface landmark is actually a vertex of the surface, its spatial relations with vertices in the neighborhood can be used to describe the geometric properties around the surface landmarks. The geometric attribute of surface landmark can be defined as the volume of the tetrahedron formed by this surface landmark and its neighboring vertices. Although the volume of the tetrahedron formed by the immediate neighbors reflects local shape information, the volumes of the tetrahedrons formed by the second or higher level neighbors can represent more global geometric properties around this surface landmark. For each surface landmark, the volumes calculated from different neighborhood layers can be stacked into an attribute vector, which characterizes the geometric features of a surface landmark from a local to a global fashion. By using this attribute vector, the similarity between two surface landmarks respectively, in MR and TRUS images, can be measured by a Euclidean distance between their normalized attribute vectors.

Next, the method 700 may including a step 740 of generating the integrated images. In some embodiments, the step 740 may include incorporating the patient-specific elastic map 714 (generated in method 600; step 330) into B-spline-based transformation determined in step 730 from the TRUS and MR image data to generate the integrated images. To incorporate the elastic map (the inhomogeneous tissue elastic property), the surface-based transformation can be weighted by the strain vector map based on the above deformation model to constrain the B-spline-based prostate-gland transformation. The prostate elastic property can be weighted into the B-spline-based tissue deformation to obtain the accurate patient-specific volumetric deformation of the prostate gland.

In some embodiments, the transformation model may be a cylindrical-based non-uniform rational B-spline. This can address problems with Cartesian coordinate B-spline models, for example, that the B-spline model is defined on a rectangular domain but the TRUS probe is cylindrical (the rectum circles the TRUS probe and the whole prostate locates in the upper half of the probe in TRUS image). This shape mismatch can cause some B-spline spans to contain few or no displacement measurements, which can cause ill-conditioning or ill-posedness.

The cylindrical coordinate B-spline model according to embodiments can reconstruct 3D displacement and strain and thus can more closely match the TRUS prostate shape than the Cartesian model. In the cylindrical B-spline model according to embodiments, the spline basis functions can be oriented radially, circumferentially, and longitudinally. This arrangement can enforce smoothness in the circumferential (shear deformation), radial (transverse deformation) and longitudinal (longitudinal deformation) directions. In contrast, Cartesian models can enforce smoothness in the x, y and z directions, which do not correspond to the anatomical structure in the TRUS prostate image. This displacement field can be described in a cylindrical coordinate system, whose origin is at the centroid of the prostate probe and the z-axis is perpendicular to the transverse imaging planes.

In some embodiments, the TRUS and the pre-operative images may be registered/integrated according to other methods.

In some embodiments, the steps of the methods may be performed over a wired, wireless, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

While the disclosure has been described in detail with reference to exemplary embodiments, those skilled in the art will appreciate that various modifications and substitutions may be made thereto without departing from the spirit and scope of the disclosure as series forth in the appended claims. For example, elements and/or features of different exemplary embodiments may be combined with each other and/or substituted for each other within the scope of this disclosure and appended claims.

What is claimed is:

1. A computer-implemented method for generating an integrated image of a prostate of a patient, comprising:
   acquiring a reference set of one or more Transrectal Ultrasound ("TRUS") images of the patient at a reference probe position using an ultrasound probe;
   causing the ultrasound probe to move to a plurality of probe positions in a direction relative to the reference probe position and the patient;
   acquiring a first set of one or more TRUS images of the patient at each of the plurality of probe positions using the ultrasound probe;

generating strain data based on a comparison of the reference set of one or more TRUS images for the reference probe position and the first set of one or more TRUS images at each of the plurality of probe positions; and the strain data representing a comparison of a strain value of each voxel with respect to each of the plurality of probe positions; and determining, by a processor, a range of probe positions based on the strain data for placement of the ultrasound probe with respect to the patient for a second set of one or more TRUS images;

the range of probe positions defining an area in which strain values are linear;

the range of probe positions including a first probe position, a second probe position, and one or more additional probe positions between the first probe position and the second probe position;

acquiring the second set of one or more TRUS images of the patient using the ultrasound probe at each probe position of the range;

generating a patient specific biomechanical model based on the second set of one or more TRUS images; and integrating the patient specific biomechanical model, the second set of one or more TRUS images and MR images to generate an integrated image of the prostate.

2. The method according to claim 1, wherein the patient specific biomechanical model is an elastic model.

3. The method according to claim 1, wherein:
the second set of one or more TRUS images includes one or more 3D TRUS images; and
the generating the patient specific biomechanical model includes:
mapping the one or more TRUS images of the second set for each of the one or more additional probe positions and the second probe position to one or more TRUS images of the second set for the first probe position to generate deformation maps;
generating additional strain data from the deformation maps; and
generating the patient specific biomechanical model based on the additional strain data.

4. The method according to claim 1, wherein:
the second set of one or more TRUS images includes one or more 3D TRUS images;
the integrating the patient specific biomechanical model, the second set of one or more TRUS images and the MR images to generate the integrated image of the prostate includes:
segmenting the second set of TRUS images and the MR images to respectively determine a TRUS prostate surface and a MR prostate surface;
registering the TRUS prostate surface and the MR prostate surface to determine a B-spline based transformation; and
incorporating the patient specific biomechanical model into the B-spline based transformation to generate the integrated images.

5. The computer-implemented method according to claim 1, wherein:
the reference set of one or more TRUS images and the first set of TRUS images are one or more 2D TRUS images; and
the second set of one or more TRUS images are one or more 3D TRUS images.

6. The computer-implemented method according to claim 1, wherein the second set of one or more TRUS images is one or more 3D TRUS images.

7. A system for generating an integrated image of a prostate of a patient, comprising:
an ultrasound system including an ultrasound probe, an ultrasound stepper configured to hold and move the ultrasound probe and an image acquisition device configured to acquire 2D and 3D TRUS images; and
a processor and a memory, wherein the processor is configured to:
acquire a reference set of one or more Transrectal Ultrasound ("TRUS") images of the patient at a reference probe position using an ultrasound probe;
cause the ultrasound probe to move to a plurality of probe positions in a direction relative to the reference probe position and the patient;
acquire a first set of one or more TRUS images at each of the plurality of probe positions of the patient using the ultrasound probe;
generate strain data based on a comparison of the reference set of one or more TRUS images for the reference probe position and the first set of one or more TRUS images at each of the plurality of probe positions; and
the strain data representing a comparison of a strain value of each voxel with respect to each of the plurality of probe positions; and
determine a range of probe positions based on the strain data for placement of the ultrasound probe with respect to the patient for a second set of one or more TRUS images;
the range of probe positions defining an area in which strain values are linear;
the range of probe positions including a first probe position, a second probe position, and one or more probe positions between the first probe position and the second probe position;
acquire the second set of TRUS images of the patient at each probe position of the range using the ultrasound probe;
generate a patient specific biomechanical model based on the second set of one or more TRUS images; and
integrate the patient specific biomechanical model, the second set of one or more TRUS images and MR images to generate an integrated image of the prostate.

8. The system according to claim 7, wherein the patient specific biomechanical model is an elastic model.

9. The system according to claim 7, wherein:
the second set of one or more TRUS images includes one or more 3D TRUS images;
the generation of the patient specific biomechanical model includes:
map TRUS images of the second set for each of the one or more probe positions and the second probe position to TRUS images of the second set for the first probe position to generate deformation maps;
generate additional strain data from the deformation maps; and
generate the patient specific biomechanical model based on the additional strain data.

10. The system according to claim 7, wherein:
the second set of one or more TRUS images includes one or more 3D TRUS images;

the integration of the patient specific biomechanical model, the second set of one or more TRUS images and the MR images to generate an integrated image of the prostate includes:
segment the second set of one or more TRUS images and the MR images to respectively determine a TRUS prostate surface and a MR prostate surface;
register the TRUS prostate surface and the MR prostate surface to determine a B-spline based transformation; and
incorporate the patient specific biomechanical model into the B-spline based transformation to generate the integrated images.

11. The system according to claim 7, wherein:
the reference set of one or more TRUS images and the first set of TRUS images are one or more 2D TRUS images; and
the second set of one or more TRUS images are one or more 3D TRUS images.

12. The system according to claim 7,
wherein the second set of one or more TRUS images is one or more 3D TRUS images.

13. A non-transitory computer-readable medium storing instructions for generating an integrated image of a prostate of a patient, the instructions comprising:
acquiring a reference set of one or more Transrectal Ultrasound ("TRUS") images of the patient at a reference probe position using an ultrasound probe;
causing the ultrasound probe to move to a plurality of probe positions in a direction relative to the reference probe position and the patient;
acquiring a first set of one or more TRUS images of the patient at each of the plurality of probe positions using the ultrasound probe;
generating strain data based on a comparison of the reference set of one or more TRUS images for the reference probe position and the first set of one or more TRUS images at each of the plurality of probe positions; and
the strain data representing a comparison of a strain value of each voxel with respect to each of the plurality of probe positions; and
determining a range of probe positions for placement based on the strain data for the placement of the ultrasound probe with respect to the patient for a second set of one or more TRUS images;
the range of probe positions defines an area in which strain values are linear;
the range of probe positions including a first probe position, a second probe position, and one or more additional probe positions between the first probe position and the second probe position;
acquiring the second set of one or more TRUS images of the patient at each probe position of the range using the ultrasound probe;
generating a patient specific biomechanical model based on the second set of one or more TRUS images; and
integrating the patient specific biomechanical model, the second set of one or more TRUS images and MR-images to generate an integrated image of the prostate.

14. The medium according to claim 13, wherein the patient specific biomechanical model is an elastic model.

15. The medium according to claim 13, the instructions further comprising:
displaying the integrated image.

16. The non-transitory computer-readable medium according to claim 13, wherein:
the reference set of one or more TRUS images and the first set of TRUS images are one or more 2D TRUS images; and
the second set of one or more TRUS images is one or more 3D TRUS images.

17. The non-transitory computer-readable medium according to claim 13,
wherein the second set of one or more TRUS images is one or more 3D TRUS images.

* * * * *